(12) United States Patent
White et al.

(10) Patent No.: US 11,881,289 B2
(45) Date of Patent: Jan. 23, 2024

(54) VIRTUAL ASSISTANT/CHATBOT TO IMPROVE CLINICAL WORKFLOWS FOR HOME RENAL REPLACEMENT THERAPIES

(71) Applicants: BAXTER INTERNATIONAL INC., Deerfield, IL (US); BAXTER HEALTHCARE SA, Glattpark (CH)

(72) Inventors: James Mitchell White, Grayslake, IL (US); Isaac Dean Martis, Chicago, IL (US); Brian James Connell, Evanston, IL (US); Kent Alan Williams, Chicago, IL (US); Judy Danek, South Milwaukee, WI (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 264 days.

(21) Appl. No.: 17/551,608

(22) Filed: Dec. 15, 2021

(65) Prior Publication Data
US 2023/0187031 A1 Jun. 15, 2023

(51) Int. Cl.
*G16H 10/20* (2018.01)
*G10L 15/22* (2006.01)
(Continued)

(52) U.S. Cl.
CPC ............ *G16H 10/20* (2018.01); *G10L 15/22* (2013.01); *G10L 15/26* (2013.01); *H04L 51/02* (2013.01);
(Continued)

(58) Field of Classification Search
CPC ........ G16H 10/20; G16H 20/00; G10L 15/22; G10L 15/26; G10L 2015/223; H04L 51/02; H04L 67/10
See application file for complete search history.

(56) References Cited

U.S. PATENT DOCUMENTS

2020/0118164 A1* 4/2020 DeFrank ............ G06Q 30/0269
2022/0392621 A1* 12/2022 George .................. G16H 20/60

FOREIGN PATENT DOCUMENTS

CN 102185882 A * 9/2011

OTHER PUBLICATIONS

"Didgebridge Alliance Offers Mobile-Video-Tech Solution to Opioid-Abuse Crisis." GlobeNewswire. Mar. 13, 2018: NA (Year: 2018).*

* cited by examiner

*Primary Examiner* — Linh Giang Le
(74) *Attorney, Agent, or Firm* — K&L Gates LLP

(57) ABSTRACT

A virtual assistant/chatbot to improve clinical workflow for home renal replacement therapies is disclosed herein. A virtual assistant/chatbot includes a patient-facing user interface configured to enable a patient to engage in a virtual chat session by typing, speaking, or otherwise providing information regarding a patient request or issue related to their renal replacement therapy. The virtual assistant/chatbot also includes a backend server-based system configured to provide logic to respond to a patient's requests. The logic defines a sequence of questions and answers for resolving patient queries. The sequence of assistant/chatbot questions and patient answers may be configured in a node arrangement such that certain patient answers/requests lead to additional questions for additional information from a patient. The virtual assistant/chatbot is configured to answer patient requests automatically or determine if the patient request is to be immediately addressed by a clinician or later through a phone call, text, or email communication.

20 Claims, 6 Drawing Sheets

(51) Int. Cl.
 *G10L 15/26* (2006.01)
 *H04L 51/02* (2022.01)
 *H04L 67/10* (2022.01)
(52) U.S. Cl.
 CPC ........ *H04L 67/10* (2013.01); *G10L 2015/223* (2013.01)

VIRTUAL ASSISTANT/CHATBOT TO IMPROVE CLINICAL WORKFLOWS FOR HOME RENAL REPLACEMENT THERAPIES

BACKGROUND

Some dialysis therapies (e.g., renal replacement therapies) can be self-administered at home by a patient. The dialysis therapies can include automated peritoneal dialysis ("APD"), continuous ambulatory peritoneal dialysis ("CAPD"), and hemodialysis ("HD"). For these self-administered therapies, a home nurse typically trains a patient to perform the therapy themselves. The home nurse is also responsible for responding to patient inquiries and other non-planned interactions that are outside of regularly scheduled clinic visits. For instance, a new patient may call the nurse if they have a question related to the administration of a therapy, such as how to order a certain component (such as dialysis fluid bags or disposable cassettes and transfer sets) or how to react to a certain alarm on a dialysis machine. In addition to these non-urgent inquiries, in some cases patients may call the nurse with a more urgent issue, such as when they are experiencing a complication or symptoms of peritonitis. While certain tools exist to answer many inquiries, such as searchable online databases, the most comfortable method for patients, many of whom are elderly, is to use the phone to interact with the nurse. As dialysis therapy takes place daily, a home nurse must be very responsive, even with non-urgent requests, to insure that these issues and inquiries do not delay a patient's dialysis therapy.

There are two extreme behaviors of dialysis patients with respect to their interactions with a home nurse. At one extreme, a patient does not want to bother the nurse even for relatively serious situations. These types of patients may let an urgent issue, such as peritonitis, go for too long prior to escalating the issue with the nurse. This can lead to infrequent but major complications if issues are not self-identified early. At the other extreme, certain patients call their nurse excessively, multiple times a week. In these cases, the patients may not have confidence to perform their therapy and sometimes just want additional psychosocial support.

Typically during the day, a nurse is tasked with training new patients and interacting with patients in a clinic. In some cases, unplanned calls from home dialysis patients may interrupt the nurse's workflow or scheduled tasks. In other cases, the home nurse may not be available to answer their phone directly if a home patient calls. Some clinics have an administrative assistant to answer patient inquiry calls, but these assistants are not medically trained and are not always available. In small dialysis clinics, one nurse may also work in other care areas, which means it may be hours to days before they can attend to patient calls and requests. Most clinics have a nurse's telephone line go directly to voicemail, such that the nurse responds to these voice mails after "regular" office hours.

Unfortunately for schedule planners, nurses spend a significant amount of time responding to unplanned patient interactions. First, the unplanned interactions require time for the nurse to determine an urgency of the interaction. Then, the nurse has to dedicate time to follow up, even for simple answers to questions or to let a patient know they have received their request. The total time responding to unplanned patient interactions can be up to ten hours/week.

A need accordingly exists for a system that offloads at least some of the unplanned interactions with home dialysis patients.

SUMMARY

A virtual assistant/chatbot to improve clinical workflow for home renal replacement therapies is disclosed herein. The virtual assistant/chatbot includes a patient-facing user interface that may be provided by a dialysis machine or an application (e.g., an App) on a smartphone or tablet. The patient-facing user interface is configured to enable a patient to engage in a virtual chat session by typing, speaking, or otherwise providing information regarding a patient request or issue related to their renal replacement or dialysis therapy. The virtual assistant/chatbot also includes a backend server-based system configured to provide logic to respond to a patient's requests. The logic may be defined by instructions stored in a memory device or a data structure that defines a logical sequence of questions and answers for resolving patient queries. The sequence of assistant/chatbot questions and patient answers may be configured in a node arrangement such that certain patient answers/requests lead to additional assistant/chatbot questions for additional information from a patient. However, instead of relying on answers from a patient for all of the assistant/chatbot questions, at least some of the assistant/chatbot questions may be determined automatically (or at least partially) using medical device data from a medical device (e.g., a dialysis machine) or contained within a patient's electronic medical record.

The logic described herein is configured to categorize, prioritize, and/or escalate a patient's request to better manage a workload of nurses and other dialysis clinicians. For example, the virtual assistant/chatbot logic described herein is configured to automatically respond to a patient's inquiry or determine whether the patient's inquiry is to be routed to a primary clinician for more specific-medical follow up. The virtual assistant/chatbot logic described herein is also configured to determine whether a patient's inquiry is to be routed to a voicemail box, virtual message box, email inbox, and/or answering service of a nurse (e.g., an at-home nurse) for lower priority issues or instead connected directly with the nurse for a more urgent medical emergency. The virtual assistant/chatbot logic described herein is also configured to determine whether a patient's inquiry is to be routed to a manufacturer of the dialysis machine (or other medical device) to resolve technical issues, reoccurring alarms, or reorder dialysis consumables such as dialysis fluid bags.

The example virtual assistant/chatbot logic is configured to reduce personal interactions between patients and nurses for relatively simple issues. Additionally, the virtual assistant/chatbot logic is configured to triage incoming patient interactions to appropriate communication routes to ensure only critical emergencies are immediately brought to the attention of clinicians and nurses. The example virtual assistant/chatbot logic accordingly provides an automated system that increases patient engagement with their dialysis treatment, thereby providing better clinical outcomes.

Patients that do not want to bother nurses may use the virtual assistant/chatbot more than their prior interactions knowing they are not being a disruption. While a nurse or clinician may periodically interact with these patients as needed, the virtual assistant/chatbot logic identifies more urgent requests, enabling nurses to schedule less urgent discussions for a time that fits within their schedule and is convenient to the patient. The virtual assistant/chatbot logic accordingly helps improve patient compliance with dialysis treatments while improving the chances that more severe medical conditions, such as peritonitis or catheter displacement are resolved sooner.

Additionally, for patients that initiate more request interactions, the virtual assistant/chatbot logic provides a screen to ensure the specific patient inquiry is routed to the most appropriate information source or communication medium. This configuration ensures one patient does not disrupt a nurse's schedule on a daily basis but instead only triggers a nurse's attention for more serious issues. Further, as these patients may expect more personal interaction, the virtual assistant/chatbot acquires sufficient information during initial patient communications to enable a nurse or other clinician to respond as appropriate with the needed information.

Overall, the virtual assistant/chatbot logic described herein may reduce clinician disruptions by as much as 80%. While clinicians may still have to respond to 50%-75% of patient inquiries, these inquiries are queued in a communication system that enables a clinician to respond as their schedule or workflow permits. Over the course of a year, the example virtual assistant/chatbot logic may save a clinician over 200 hours in handling non-critical disruptions.

The example virtual assistant/chatbot logic and methodology of the present disclosure is applicable, for example, to fluid delivery for plasmapherisis, hemodialysis ("HD"), hemofiltration ("HF") hemodiafiltration ("HDF"), and continuous renal replacement therapy ("CRRT") treatments. The medical fluid data transfer system described herein is also applicable to peritoneal dialysis ("PD"), intravenous drug delivery, and nutritional fluid delivery. These modalities may be referred to herein collectively or generally individually as a medical fluid delivery or treatment.

The above modalities may be provided by a medical fluid delivery machine that houses components needed to deliver medical fluid, such as one or more pumps, valves, heaters (if needed), online medical fluid generation equipment (if needed), sensors, such as any one, or more, or all of pressure sensors, conductivity sensors, temperature sensors, air detectors, blood leak detectors, and the like, user interfaces, and control units, which may employ one or more processors and memory to control the above-described equipment. The medical fluid delivery machine may also include one or more filters, such as a dialyzer or hemofilter for cleansing blood and/or an ultrafilter for purifying water, dialysis fluid, or other fluid.

The medical fluid delivery machine and the medical fluid data transfer system and methodology described herein may be used with home-based machines. For example, the systems may be used with home HD, HF or HDF machines, which are operated at the patient's convenience. One such home system is described in U.S. Pat. No. 8,029,454 ("the '454 Patent"), issued Oct. 4, 2011, entitled "High Convection Home Hemodialysis/Hemofiltration And Sorbent System", filed Nov. 4, 2004, assigned to the assignees of the present application. Other such home systems are described in U.S. Pat. No. 8,393,690 ("the '690 Patent"), issued Mar. 12, 2013, entitled "Enclosure for a Portable Hemodialysis System", filed Aug. 27, 2008. The entire contents of each of the above references are incorporated herein by reference and relied upon.

As described in detail below, the example virtual assistant/chatbot logic and methodology of the present disclosure may operate within an encompassing platform or system that may include many machines comprising many different types of devices, patients, clinicians, doctors, service personnel, electronic medical records ("EMR") databases, a website, a resource planning system handling data generated via the patient and clinician communications, and business intelligence. The example virtual assistant/chatbot logic and methodology of the present disclosure operates seamlessly within the overall system and without contravening its rules and protocols.

In light of the disclosure herein and without limiting the disclosure in any way, in a first aspect of the present disclosure, which may be combined with any other aspect listed herein unless specified otherwise, a virtual assistant/chatbot system to improve clinical workflows for home renal replacement therapies includes an interface communicatively coupled to a network. The interface is configured to communicate with an application on user devices or an interface for medical devices. The system also includes a memory device storing a patient inquiry triage data structure for a virtual assistant or chatbot. The data structure includes a plurality of potential issues related to dialysis or operation of a medical device, each issue including a hierarchy of questions and possible answers that lead to a response action. The response action includes a direct communication connection with a clinician and a communication connection with a voicemail system, a person-to-person chat system, or an email system. The system further includes a processor communicatively coupled to the interface and the memory device. The processor is configured to receive an inquiry message from the application on a user device or the interface of a medical device and provide an interactive session using the virtual assistant or chatbot to progress through the hierarchy of questions with one or more prompts to receive further information until a response action is identified. When the response action is related to direct communication, the processor is configured to determine an address or number of a clinician device and cause a communication session to be initiated between the application on the user device or the interface of the medical device and the clinician device. When the response action is related to the voicemail system, the person-to-person chat system, or the email system, the processor is configured to determine an account of a clinician and enable the patient to use the application on the user device or the interface of the medical device to enter a request message for a clinician.

In accordance with a second aspect of the present disclosure, which may be used in combination with any other aspect listed herein unless stated otherwise, the processor is further configured to incorporate at least some of the further information from the interactive session with the request message for the clinician.

In accordance with a third aspect of the present disclosure, which may be used in combination with any other aspect listed herein unless stated otherwise, the processor, the memory device, and the interface are located in a cloud-computing environment.

In accordance with a fourth aspect of the present disclosure, which may be used in combination with any other aspect listed herein unless stated otherwise, the inquiry message and the further information is received as speech, and the processor is configured to convert the speech to text.

In accordance with a fifth aspect of the present disclosure, which may be used in combination with any other aspect listed herein unless stated otherwise, the processor is further configured to receive a clinician response message from the account of the clinician for the voicemail system, the person-to-person chat system, or the email system, and transmit the clinician response message to the application on the user device or the interface of the medical device.

In accordance with a sixth aspect of the present disclosure, which may be used in combination with any other aspect listed herein unless stated otherwise, the response action further includes an automated response action, and when the response action is related to the automated response action, the processor is configured to transmit information indicative of the automated response action to the application on the user device or the interface of the medical device.

In accordance with a seventh aspect of the present disclosure, which may be used in combination with any other aspect listed herein unless stated otherwise, the automated response action includes at least one of an answer from a patient guide, an answer about an order for a medical device consumable item, an answer related to an operation of the medical device, or a preprogrammed answer related to general patient health or medical conditions.

In accordance with an eighth aspect of the present disclosure, which may be used in combination with any other aspect listed herein unless stated otherwise, the response action further includes a medical device manufacturer response action, and when the response action is related to the medical device manufacturer response action, the processor is configured to determine an address or number of a manufacturer device and cause a communication session to be initiated between the application on the user device or the interface of the medical device and the manufacturer device.

In accordance with a ninth aspect of the present disclosure, which may be used in combination with any other aspect listed herein unless stated otherwise, the medical device manufacturer response action relates to at least one of reordering consumables for the medical device, a technical issue with the medical device, or an operational issue with the medical device.

In accordance with a tenth aspect of the present disclosure, which may be used in combination with any other aspect listed herein unless stated otherwise, the medical device includes at least one of a peritoneal dialysis machine, a hemodialysis machine, a continuous renal replacement therapy ("CRRT") machine, an infusion pump, or a patient-controlled analgesia ("PCA") machine.

In accordance with an eleventh aspect of the present disclosure, which may be used in combination with any other aspect listed herein unless stated otherwise, the processor is further configured to access at least one of treatment data from the medical device or patient data related to the patient from an electronic medical record after receiving the inquiry message, and use at least some of the treatment data or the patient data as answers for progressing through the hierarchy of questions as part of the interactive session.

In accordance with a twelfth aspect of the present disclosure, which may be used in combination with any other aspect listed herein unless stated otherwise, the processor is further configured to access at least one of treatment data from the medical device or patient data related to the patient from an electronic medical record after receiving the inquiry message, and include at least some of the treatment data or the patient data with the request message for the clinician.

In accordance with a thirteenth aspect of the present disclosure, which may be used in combination with any other aspect listed herein unless stated otherwise, the treatment data includes at least one of (i) treatment parameters for a dialysis prescription, (ii) results from performing one or more dialysis treatments, (iii) diagnostic information related to the medical device, or (iv) a current status of the medical device, and the patient data includes at least one of electronic medical record information, laboratory results, electronic clinician notes, previous medical diagnoses, patient physiological data, or patient demographic data.

In accordance with a fourteenth aspect of the present disclosure, which may be used in combination with any other aspect listed herein unless stated otherwise, a hierarchy of the patient inquiry triage data structure is configured to be modified based on protocols of a hospital system or clinic.

In accordance with a fifteenth aspect of the present disclosure, which may be used in combination with any other aspect listed herein unless stated otherwise, a virtual assistant/chatbot method to improve clinical workflows for home renal replacement therapies includes receiving, in a processor, an inquiry message from an application on a user device or an interface of a medical device and providing, via the processor, an interactive session using a virtual assistant or chatbot to progress through a hierarchy of questions with one or more prompts to receive further information until a response action is identified, instructions for the virtual assistant or chatbot being stored in a memory device that also stores a patient inquiry triage data structure for the virtual assistant or chatbot The data structure includes a plurality of potential issues related to dialysis or operation of a medical device, each issue including the hierarchy of questions and possible answers that lead to a response action. The response action includes a direct communication connection with a clinician and a communication connection with a voicemail system, a person-to-person chat system, or an email system. The method also includes when the response action is related to direct communication, determining, via the processor, an address or number of a clinician device and causing a communication session to be initiated between the application on the user device or the interface of the medical device and the clinician device. The method further includes when the response action is related to the voicemail system, the person-to-person chat system, or the email system, determining an account of a clinician and enabling the patient to use the application on the user device or the interface of the medical device to enter a request message for a clinician.

In accordance with a sixteenth aspect of the present disclosure, which may be used in combination with any other aspect listed herein unless stated otherwise, the method further includes incorporating, via the processor, at least some of the further information from the interactive session with the request message for the clinician.

In accordance with a seventeenth aspect of the present disclosure, which may be used in combination with any other aspect listed herein unless stated otherwise, the inquiry message and the further information is received as speech, and the method includes converting the speech to text.

In accordance with an eighteenth aspect of the present disclosure, which may be used in combination with any other aspect listed herein unless stated otherwise, the method further includes receiving, in the processor, a clinician response message from the account of the clinician for the voicemail system, the person-to-person chat system, or the email system, and transmitting, via the processor, the clinician response message to the application on the user device or the interface of the medical device.

In accordance with a nineteenth aspect of the present disclosure, which may be used in combination with any other aspect listed herein unless stated otherwise, the response action further includes an automated response action, and when the response action is related to the automated response action, the method further includes transmitting information indicative of the automated response action to the application on the user device or the interface of the medical device.

In accordance with a twentieth aspect of the present disclosure, which may be used in combination with any other aspect listed herein unless stated otherwise, the automated response action includes at least one of an answer from a patient guide, an answer about an order for a medical device consumable item, an answer related to an operation of the medical device, or a preprogrammed answer related to general patient health or medical conditions.

In accordance with a twenty-first aspect of the present disclosure, which may be used in combination with any other aspect listed herein unless stated otherwise, the method further includes accessing, via the processor, at least one of treatment data from the medical device, a prescribed therapy or program, or patient related to the patient from an electronic medical record after receiving the inquiry message, and including, via the processor at least some of the medical device data, the prescribed therapy or program, or the medical information with the request message for the clinician, wherein the prescribed therapy or program includes treatment parameters for a dialysis prescription, treatment data includes at least one of (i) results from performing one or more dialysis treatments, (ii) diagnostic information related to the medical device, or (iii) a current status of the medical device, and wherein the patient data includes at least one of electronic medical record information, laboratory results, electronic clinician notes, previous medical diagnoses, patient physiological data, or patient demographic data.

In a twenty-second aspect of the present disclosure, any of the structure, functionality, and alternatives disclosed in connection with any one or more of FIGS. 1 to 6 may be combined with any other structure, functionality, and alternatives disclosed in connection with any other one or more of FIGS. 1 to 6.

In light of the present disclosure and the above aspects, it is therefore an advantage of the present disclosure to a system that uses virtual assistant/chatbot logic to automatically triage patient medical-related requests.

It is another advantage of the present disclosure to use information provided by a patient during an interactive session with virtual assistant/chatbot logic to determine if their inquiry is less urgent, semi-urgent, or critically urgent and provide an appropriate response action based on the level of urgency.

It is a further advantage of the present disclosure to use patient data and/or treatment data to more quickly converge upon a response action for a patient inquiry.

It is still a further advantage of the present disclosure to use patient data and/or treatment data as part of content for a response action for a patient inquiry.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
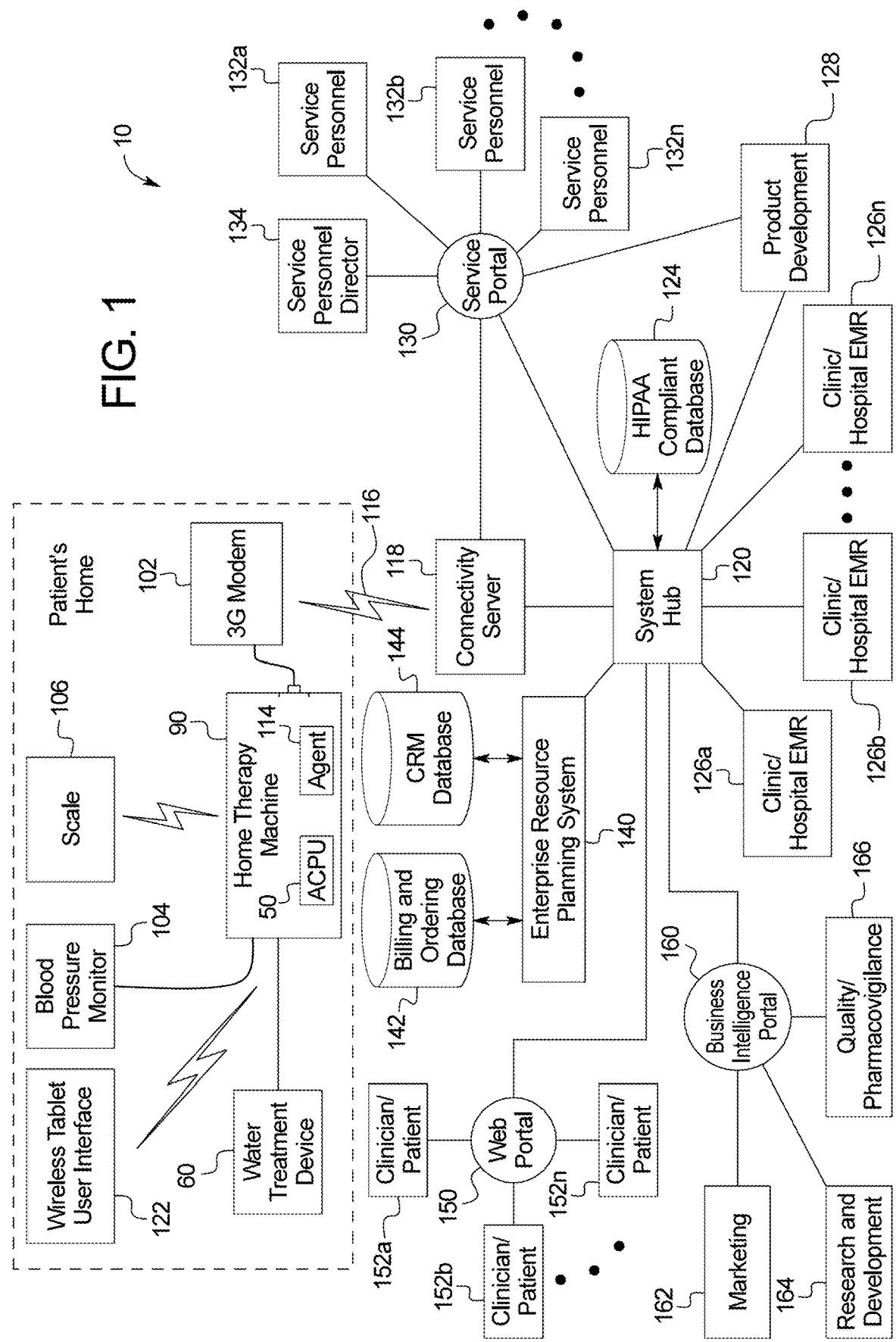
FIG. 1 is a schematic view illustrating a medical system that includes at least one medical fluid delivery machine, according to an embodiment of the present disclosure.

A virtual assistant/chatbot to improve clinical workflow for home renal replacement therapies is disclosed herein. The virtual assistant/chatbot is configured to provide automated triage of incoming patient requests to determine when a response can be provided in an automated manner and when a response is needed from a clinician or manufacturer of a medical device. The virtual assistant/chatbot ensures that patient requests are quickly attended to while reducing the personal burden of clinical staff. The virtual assistant/chatbot is configured to accordingly improve patient engagement and treatment compliance by ensuring that patient requests are handled in the most efficient and timely manner possible.

As discussed herein, the virtual assistant/chatbot includes a patient-facing user interface that may be provided by a dialysis machine or an application (e.g., an App) on a smartphone or tablet. The patient-facing user interface is configured to enable a patient to engage in a virtual chat session by typing, speaking, or otherwise providing information regarding a question or issue related to their renal replacement or dialysis therapy. The virtual assistant/chatbot also includes a backend server-based system configured to provide logic to respond to a patient's requests. The logic may be defined by instructions stored in a memory device or a data structure that defines a logical sequence of questions and answers for resolving patient queries.

Reference is made herein to prescribed therapies or programs and corresponding treatments. A prescribed therapy or program corresponds to one or more parameters that define how a medical fluid delivery machine is to operate to administer a treatment to a patient. For a peritoneal dialysis therapy, the parameters may specify an amount (or rate) of fresh dialysis fluid to be pumped into a peritoneal cavity of a patient, an amount of time the fluid is to remain in the patient's peritoneal cavity (i.e., a dwell time), and an amount (or rate) of used dialysis fluid and ultrafiltration ("UF") that is to be pumped or drained from the patient after the dwell period expires. For a treatment with multiple cycles, the parameters may specify the fill, dwell, and drain amounts for each cycle and the total number of cycles to be performed during the course of a treatment (where one treatment is provided per day or separate treatments are provided during the daytime and during nighttime). In addition, the parameters (or device programs) may specify dates/times/days (e.g., a schedule) in which treatments are to be administered by the medical fluid delivery machine. Further, parameters of a prescribed therapy may specify a total volume of dialysis fluid to be administered for each treatment in addition to a concentration level of the dialysis fluid, such as a dextrose level.

While a prescribed therapy may specify parameters for each treatment provided by a medical fluid delivery machine, the treatment data reported by the machine may differ. As discussed herein, treatment data refers to data generated by a medical fluid delivery machine that is indicative of measured, detected, or determined parameter values. For example, while a prescribed therapy may specify that a treatment is to comprise five separate cycles, each with a 45-minute dwell time, a medical fluid delivery machine may administer a treatment where fewer cycles are provided, each with a 30-minute dwell time. The difference from the prescribed parameters may be due to a patient overriding the therapy program or stopping a treatment prematurely. The medical fluid delivery machine monitors how the treatment is administered and accordingly provides parameters that are indicative of the operation. The parameters for the treatment data may include, for example, a total amount of dialysis fluid administered to a patient, a number of cycles operated, a fill amount per cycle, a dwell time per cycle, a drain time/amount per cycle, an estimated amount of UF removed, a treatment start time/date, and/or a treatment end time/date. The treatment data may also include calculated parameters, such as a fill rate and a drain rate, determined by dividing the amount of fluid pumped by the time spent pumping. The treatment data may further include an identification of an alarm that occurred during a treatment, a duration of the alarm, a time of the alarm, an event associated with the alarm, and/or an indication as to whether the issue that caused the alarm was resolved or whether the alarm was silenced. The treatment data may also include event data, such as times/durations that a medical fluid delivery machine was stopped/paused or a time when a treatment ended.

In addition to treatment data, the medical fluid delivery system may use patient data. As disclosed herein, patient data corresponds to medical data that may be contained within an electronic medical record ("EMR"), such as medical history, prescription history, current/past treatments, laboratory results, etc. Additionally or alternatively, the patient data may include demographic data that may be provided by a clinician/patient, specified within a prescribed therapy or program, and/or provided via patient registration. The demographic data may include a patient age, a gender, a patient mobility level, a patient's renal condition, a prescription history, etc. In some embodiments, the patient data may include an identifier, which enables the medical fluid delivery system to store the received data in an appropriate patient record located in a database. The identifier may include a patient identifier, a patient name, and/or an identifier of the medical fluid delivery system.

As discussed herein, the medical fluid delivery machine is located in a residence of a patient. However, in some embodiments, the medical fluid delivery machine may be located at a full-service medical facility and/or a self-service medical facility. In some embodiments, a patient may use a first medical fluid delivery machine that is located at their residence and use a second medical fluid delivery machine that is located at a self-service medical facility. In these embodiments, the medical fluid delivery system is configured to combine the treatment data from the first and second medical fluid delivery machines.

As disclosed herein, the virtual assistant/chatbot logic is configured to use one or more computational structures specified in a data structure that define an interaction with a patient based on one or more patient answers. It should be appreciated that virtually any data structure may be used. For example, questions, answers, and results may be stored as nodes and links in a graph database structure. In another example, questions, answers, and results may be stored in a relational, sequential, or hierarchical data structure. The linkages between answers and questions is configured to guide the virtual assistant/chatbot logic to select which subsequent action is to be performed.

The use of readily available prescribed therapies, treatment data, and/or patient data enables the virtual assistant/chatbot logic disclosed herein to more accurately and quickly identify a response action while reducing answers needed from a patient. In some instances, patient requests or questions that may initially have low context or seem unclear are more readily apparent by the virtual assistant/chatbot logic analyzing the prescribed therapies, treatment data, and/or patient data in conjunction with the request. In an example, a patient may start an interaction with the virtual assistant/chatbot logic disclosed herein by stating that they "Are Tired of this Alarm". By itself, this statement is unclear and could refer to pressure alarms, occlusion alarms, low fluid flow alarms, low battery alarms, etc. However, when the virtual assistant/chatbot logic receives such a statement in conjunction with treatment data from the medical fluid delivery machine that identifies which alarms have recently been triggered, there is a high probability that the patient is referring to these recently triggered alarms. The example virtual assistant/chatbot logic accordingly uses available data to quickly converge upon an appropriate response action without burdening a patient with excess questions and without burdening clinical staff by having to respond to every patient inquiry.

I. Medical Fluid Delivery System Embodiment

The example medical fluid delivery system disclosed herein includes one or more medical fluid delivery machines. One example of a medical fluid delivery machine is a renal failure therapy machine. Regarding renal failure therapy machines, due to various causes, a patient's renal system can fail. Renal failure produces several physiological derangements. For instance, a patient experiencing renal failure can no longer balance water and minerals or excrete daily metabolic load. Toxic end products of nitrogen metabolism (urea, creatinine, uric acid, and others) can accumulate in the patient's blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across a semi-permeable dialyzer between a patient's blood and an electrolyte solution, called dialysate or dialysis fluid, to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HEM can be performed daily, offering therapeutic benefits over in-center hemodialysis treatments, which occur typically bi- or tri-weekly. Studies have shown that frequent treatments remove more toxins and waste products than a patient receiving less frequent, but perhaps longer treatments. A patient receiving treatments more frequently does not experience as much of a down cycle compared to an in-center patient, who has built-up two or three days' worth of toxins prior to treatment. In certain areas, the closest dialysis center can be many miles from the patient's home causing door-to-door treatment time to consume a large portion of the day. HHD in contrast may take place overnight or during the day while the patient relaxes, works or is otherwise productive.

Another type of kidney failure therapy is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to enable used or spent dialysate fluid to drain from the patient's peritoneal cavity. The patient then connects the catheter to a bag of fresh dialysis fluid to infuse fresh dialysis fluid through the catheter and into the patient. The patient disconnects the catheter from the fresh dialysis fluid bag and enables the dialysis fluid to dwell within the peritoneal cavity, where the transfer of waste, toxins, and excess water takes place. After a dwell period, the patient repeats the manual dialysis procedure, for example, four times per day, each treatment lasting between an hour and six hours. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins, and excess water to take place. The source may include multiple sterile dialysis fluid bags.

APD machines pump used or spent dialysate from a patient's peritoneal cavity, though a catheter, and to a drain. As with the manual process, several drain, fill and dwell cycles occur during dialysis. A "last fill" occurs at the end of APD and remains in the peritoneal cavity of the patient until the next treatment.

Any of the above modalities performed by a machine may be run on a scheduled basis and may require a start-up procedure. For example, dialysis patients typically perform treatment on a scheduled basis specified by a prescribed therapy or program, such as every other day, daily, etc. Blood treatment machines typically require a certain amount of time before treatment for setup, for example, to run a disinfection procedure. Patients for the above modalities may lead busy lives and have projects to perform or errands to run on a day scheduled for treatment.

Much of the appeal of a home treatment for the patient revolves around the lifestyle flexibility provided by allowing a patient to perform treatment in his or her home largely according to his or her own schedule. The home medical fluid delivery machine may, however, include software timers that dictate to and constrain the patient. A home hemodialysis system may, for example, require a patient to be in immediate proximity to the home hemodialysis machine to initiate pre-treatment, during treatment, and post-treatment sequences.

In one particular example, a therapy machine may reuse certain components by disinfecting them in between treatments. The machine may employ one or more disinfection timers that require a patient or caregiver to start a treatment using the machine before the disinfection timer expires. Otherwise, the patient will have to wait until another disinfection procedure is completed before starting treatment. The therapy machine in an embodiment communicates the treatment start time deadlines via the machine's graphical user interface.

It is contemplated for the software of the system and methodology of the present disclosure to disable communication between the patient and/or caregiver and the machine whenever the machine is in a "patient connected" software state. For example, if a clinician tries to send a command to a machine currently treating a patient, the command may be intercepted by a middleware software application so that the command is not transferred to the machine. The middleware software application may then communicate back to the clinician informing that the machine is busy and not accepting communication.

The examples described herein are applicable to any medical fluid delivery system that delivers a medical fluid, such as blood, dialysis fluid, substitution fluid or and intravenous drug ("IV"). The examples are particularly well suited for kidney failure therapies, such as all forms of hemodialysis ("HD"), hemofiltration ("HF"), hemodiafiltration ("HDF"), continuous renal replacement therapies ("CRRT") and peritoneal dialysis ("PD"), referred to herein collectively or generally individually as a prescribed therapy or program. The medical fluid delivery machines may alternatively be a drug delivery or nutritional fluid delivery device, such as a large volume peristaltic type pump or a syringe pump. The machines described herein may be used in home settings. For example, a machine operating with a data transfer component may be employed with a home HD machine, which can, for example, be run at night while the patient is sleeping. The medical fluid data transfer system and methodology of the present disclosure may alternatively be used to help clinicians or nurses in hospitals and/or clinics.

Referring now to the drawings, and in particular to FIG. 1, a medical system 10 is illustrated. The example system 10 includes many medical fluid delivery machines 90 (one type of which is discussed in detail below). The machines 90 of the medical system 10 may be of a same type (e.g., all PD machines) or be of different types (e.g., a mix of HD, PD, CRRT, and medical or nutritional fluid delivery).

While a single medical fluid delivery 90 is illustrated as communicating with a connectivity server 118, the system 10 manages the operation of a plurality of medical fluid delivery systems and machines, of the same type or of different types listed above. For example, there may be M number of hemodialysis machines 90, N number of hemofiltration machines 90, O number of CRRT machines 90, P number of peritoneal dialysis machines 90, Q number of home drug delivery machines 90, and R number of nutritional or drug delivery machines 90 connected to the server 118 and operating with the system 10. The numbers M through R may be the same or different numbers, and may be zero, one, or more than one. In FIG. 1, the medical fluid delivery machine 90 is illustrated as a therapy machine 90 (the home indicated by dashed lines).

The therapy machine 90 may receive at its front end purified water from a water treatment device 60. The water treatment device 60 connects to the therapy machine 90 via an Ethernet cable, in an embodiment. The therapy machines 90 in the illustrated embodiment operates with other devices besides the water treatment device 60, such as a blood pressure monitor 104, a weigh scale, e.g., a wireless weigh scale 106, and a user interface such as a wireless tablet user interface 122. The therapy machine 90 connects to the server 118 wirelessly in one embodiment via a modem 102. Each of these components may (but does not have to be) located within the patient's home, as demarcated by the dashed lines in FIG. 1. Any one, or more, or all of the components 60, 104, 106 and 122 may communicate wired or wirelessly with the therapy machine 90. Wireless communication may be via Bluetooth™, WiFi™, Zigbee®, Z-Wave®, wireless Universal Serial Bus ("USB"), infrared, or any other suitable wireless communication technology. Alternatively, any one, or more or all of the components 60, 104, 106 and 122 may communicate with the therapy machine 90 via wired communication.

The example connectivity server 118 communicates with the medical fluid delivery machine 90 via a medical device system hub 120. The example system hub 120 enables data and information concerning each therapy machine 90 and its peripherals to travel back and forth via the connectivity server 118 between the machines 90 and the other devices that are connected to the server 118. In the illustrated embodiment, the system hub 120 is connected to a service portal 130, an enterprise resource planning system 140, a web portal 150, a business intelligence portal 160, a HIPAA compliant database 124, a product development team 128, and electronic medical records databases maintained, for example, at clinics or hospitals 126a to 126n. The connectivity server 118 and/or the portals 130, 150, and 160 may include gateway devices.

The illustrated electronic medical records ("EMR") databases may be located at clinics or hospitals 126a to 126n and store electronic information concerning patients. The system hub 120 may transmit the data collected from log files of machine 90 (e.g., treatment data) to the hospital or clinic databases 126a to 126n to merge or supplement that patient's medical records. The databases at clinics or hospitals 126a to 126n may contain patient-specific treatment and prescription data (e.g., prescribed therapies or programs), where access to such databases may be highly restricted. The example enterprise resource planning system 140 is configured to obtain and compile data generated via patient and clinician website access, such as complaints, billing information, and life cycle management information. The web portal 150 enables patients and clinics 152a to 152n treating the patients to access a website that is publicly available. The business intelligence portal 160 collects data from the system hub 120 and provides the data to marketing 162, research and development 164, and quality/pharmacovigilance 166.

It should be appreciated that the systems, methods and procedures described herein may be implemented using one or more computer programs or components. The programs of the components may be provided as a series of computer instructions on any computer-readable medium, including random access memory ("RAM"), read only memory ("ROM"), flash memory, magnetic or optical disks, optical memory, or other storage media. The instructions may be configured to be executed by a processor, which when executing the series of computer instructions, performs or facilitates the performance of all or part of the disclosed methods and procedures that are described herein.

In one embodiment, the therapy machine 90 performs a home treatment, such as home peritoneal dialysis on a patient at the patient's home, and then reports the results of that treatment (as treatment data) to the system hub 120, which may be in communication with one or more servers. As described in more detail below, the one or more servers analyze the treatment data for reporting to clinicians, doctors, and/or nurses who are responsible for managing the health and well-being of that patient.

The therapy machines 90 in an embodiment writes log files using, e.g., a Linux™ operating system. The log files document pertinent therapy machine 90 data, including peripheral device data. The log files may include any one or more of Extensible Markup Language ("XML"), comma-separated values ("CSV"), or text files. The log files are placed into a file server repository managed by software of therapy machine 90. It is also contemplated to store data at a peripheral device, e.g., water treatment device 60, which is not sent to machine 90. Such data may otherwise be obtained via the wired or wireless connection to the peripheral device or downloaded through other data connections or storage media.

In one embodiment, the therapy machine 90, e.g., via the internet, uses a connectivity service to transfer treatment data between the modem 102 and the system hub 120. Here, a dedicated line may be provided at each patient's home for connecting the therapy machine 90 to the connectivity server 118 via the modem 102. The therapy machine 90, in one embodiment, accesses the internet using a separate, e.g., 3G, 4G, or 5G, modem 102. The modem 102 may use an internet Service Provider ("ISP"), such as Vodafone™. In one implementation, a connectivity agent 114 developed by a connectivity service provider (e.g., provider of connectivity server 118) is installed onto the therapy machine 90 and run on a primary control processor ("ACPU") 50 of the machine. One suitable connectivity service is provided by Axeda™, which provides a secure managed connection 116 between medical devices and the connectivity server 118.

The example connectivity agent 114 of FIG. 1 is configured to enable the therapy machine 90 to connect to the connectivity server 118 and transfer the treatment data to and from the connectivity server 118. A connectivity service operating via the agent 114 and the server 118 ensures that the connection with the machine 90 is secure, ensures that the data correctly passes through the machine 90's firewalls, detects whether there has been a data or system crash, and ensures that the connectivity server 118 is communicating with the correct therapy machine 90.

In one embodiment, the therapy machine 90 may only connect to the connectivity server 118 when the connectivity agent 114 is turned on or activated. During treatment and post-treatment disinfection, while the machine 90 and its peripherals are functioning, the connectivity agent 114 is automatically turned off in one embodiment, which prevents the therapy machine 90 from communicating with any entity and sending or receiving data during treatment and disinfection or when machine 90 is live or running. When the therapy machine 90 is idle, e.g., after treatment and post-disinfection is complete, the ACPU 50 turns the connectivity agent 114 on, in one embodiment. In an embodiment, the connectivity agent 114 is off during treatment, and possibly pre-treatment. After treatment, the connectivity agent 114 retrieves the log files from the therapy machine 90 and transfers the treatment data to the connectivity server 118 using the connectivity service. The connectivity service routes data packets to their proper destination, but in one embodiment, does not modify, access, or encrypt the data.

In medical system 10 system of FIG. 1, the connectivity service via the connectivity server 118 may communicate data to various places via the system hub 120, such as the service portal 130, the clinics or hospitals 126a to 126n, and the web portal 150. The connectivity server 118 enables service personnel 132a to 132n and/or clinicians to track and retrieve various assets across the network, such as appropriate therapy machines 90 and 3G, 4G, or 5G modem 102, and their associated information, including machine or modem serial numbers. The connectivity server 118 may also be used to receive and provide firmware upgrades, approved by a director of service personnel 134 and obtained remotely via the service portal 130, to the authorized therapy machines 90 and associated peripherals, such as water treatment devices 60.

A. Connectivity Embodiment of the Example Medical Fluid Delivery System

Figure 2:
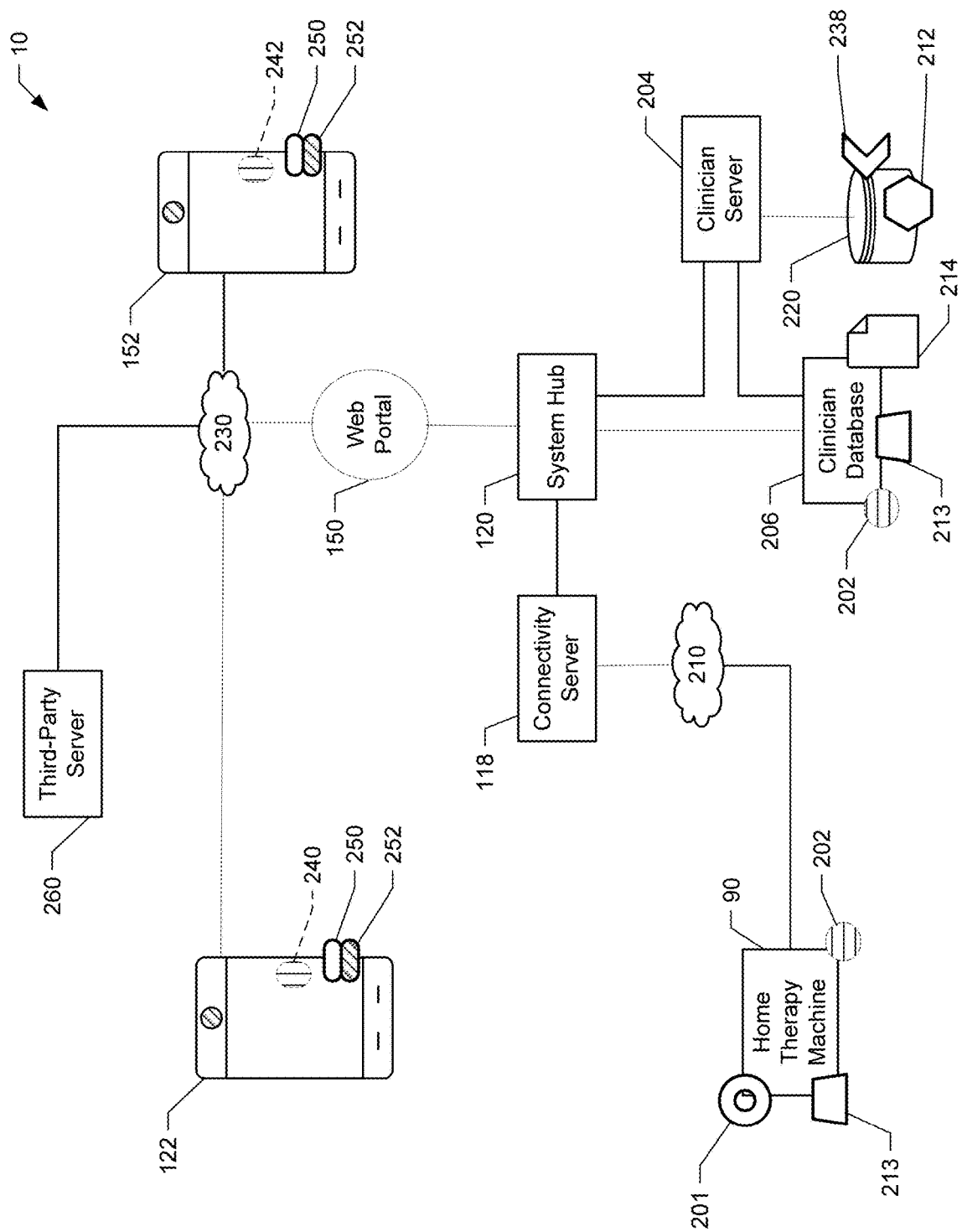
FIG. 2 is a schematic illustration of the medical system of FIG. 1 including a clinician server, according to an embodiment of the present disclosure.

FIG. 2 illustrates a diagram of the medical system 10 of FIG. 1, according to an example embodiment of the present disclosure. The example medical system 10 includes, for example, a personal mobile communication device 122 (e.g., a user device) that is operated by a patient, and a clinician device 152 that is operated by a clinician. The medical system 10 also includes a therapy machine 90 (e.g., a medical fluid delivery machine), which is similar to the respective devices discussed above in connection with FIG. 1. The personal mobile communication device 122 and the therapy machine 90 may be located, for example, at a patient's home, a self-service clinic, and/or a serviced medical clinic.

The therapy machine 90 may include any type of hemodialysis machine, peritoneal dialysis machine, CRRT machine, drug and/or nutritional fluid delivery machine, and combinations thereof. The therapy machine 90 may provide, for example continuous cycling peritoneal dialysis ("CCPD"), tidal flow automated peritoneal dialysis ("APD"), and continuous flow peritoneal dialysis ("CFPD"). The therapy machine 90 may perform drain, fill, and dwell cycles automatically, typically while a patient sleeps.

The example therapy machine 90 may also include one or more control interfaces 201 for displaying instructions and receiving control inputs from a user. The control interfaces 201 may include buttons, a control panel, and/or a touchscreen. The control interfaces 201 may also be configured to enable a user to navigate to a certain window or user interface on a screen of the therapy machine 90. The control interfaces 201 may further provide instructions for operating or controlling the therapy machine 90.

The example therapy machine 90 may receive one or more prescribed therapies or programs 202 remotely from a clinician server 204 and/or a clinician database 206. Additionally or alternatively, the therapy machine 90 may be programmed locally via the control interface 201 with a prescribed therapy or program 202. As discussed herein, a prescribed therapy 202 includes parameters that specify how the therapy machine 90 is to administer one or more scheduled treatments to a patient (e.g., the patient 12 of FIG. 1). The therapy parameters 202 may include a number of fill-dwell-drain cycles for a peritoneal dialysis therapy in addition to a duration for each phase. The therapy parameters may also include a total volume of dialysis fluid to be administered (and/or a volume of fluid to be administered per cycle), a dextrose concentration, and/or a target UF removal level. The therapy parameters 202 may also include a schedule of treatment dates and a total treatment duration. In some embodiments, the clinician server 204 may remotely update any one of the prescribed therapy parameters.

It should be appreciated that the medical system 10 may include additional medical devices such as a weight scale, a blood pressure monitor, an infusion pump (e.g., a syringe pump, a linear peristaltic pump, a large volume pump ("LVP"), an ambulatory pump, a multi-channel pump), an oxygen sensor, a respiratory monitor, a glucose meter, a blood pressure monitor, an electrocardiogram ("ECG") monitor, and/or a heart rate monitor. In other examples, the medical fluid data transfer system 90 may include fewer medical devices and/or medical devices integrated with the therapy machine 90.

As shown in FIG. 2, the therapy machine 90 is communicatively coupled to the connectivity server 118 via a network 210. As discussed above in connection with FIG. 1, the connectivity server 118 provides bidirectional communication between the therapy machine 90 and the system hub 120. The network 210 may include any wired or wireless network including the Internet, a cellular network, or combinations thereof.

The example system hub 120 is also communicatively coupled to the clinician server 204 and the clinician database 206. As described in more detail below, the clinician server 204 is configured to execute one or more instructions, routines, algorithms, applications, or programs (e.g., a virtual assistant/chatbot) 212 for determining how patient requests are to be handled. The clinician database 204 is configured to store prescribed therapies or programs 202 for each patient associated with the system 10. The clinician database 206 is also configured to store one or more records for each patient that include treatment data 213 from the respective therapy machine 90 and/or patient data 214 (e.g., a patient's EMR).

In the illustrated example, the clinician server 204 is communicatively coupled to a memory device 220 that stores the one or more instructions, routines, algorithms, applications, or programs for executing the virtual assistant/ chatbot logic 212. The memory device 220 may also store one or more data structures and/or instructions 222 that define an automated interaction with a patient to for determining a response action 238. The one or more instructions, routines, algorithms, applications, or programs for executing the virtual assistant/chatbot logic 212 and/or the one or more data structures and/or instructions 222 may include machine-readable instructions, that when executed by one or more processors of the clinician server 204, cause the clinician server 204 to perform the operations described herein.

As discussed herein, a response action 238 is an operation carried out by the clinician server 204 based on a level of response needed for a patient inquiry or request. The response action 238 may include determining that an automated response is appropriate and transmitting one or more messages to the patient with technical/medical information (as the response action 238) for addressing a low or less-urgent patient's inquiry. The response action 238 may also include determining that the patient's inquiry has a medium urgency and that the inquiry should be transmitted in one or more messages (as the response action 238) to a voicemail system, a person-to-person chat system, or an email system of a clinician. In some embodiments, the clinician server 204 determines which clinician is to receive the message based on a name provided by the patient, a documented past relationship with the patient (as provided in the patient data 214), or based on a role or responsibility in relation to the request. After identifying the clinician, the clinician server 204 determines a corresponding account and transmits the response action 238 to the account. In some embodiments, the clinician server 204 prompts the patient to enter their query. Additionally or alternatively, the clinician server 204 uses information from an interaction of the patient with the virtual assistant/chatbot 212 to automatically create content for the response action 238. In this manner, not only is the data 202, 213, and 214 used for navigating the patient interaction, it may be used in conjunction with patient responses for conveying specific request information to the clinician.

In an example, a patient may initiate an inquiry by starting through an application 140 on their personal mobile communication device 122 that they cannot resolve an alarm. In response, the clinician server 204 uses the virtual assistant/chatbot 212 to determine from the patient what actions they have already tried to resolve the alarm. Further, the clinician server 204 locates relevant treatment data 213 to determine the type of alarm and/or recent dates/times the alarm was activated. Based on this collection of data, the clinician server 204 determines that the patient inquiry is a medium-level (because intermittent alarms are annoying but not critical), and accordingly prompts the patient to enter information for the response action 238 and/or uses at least some of the patient responses to the virtual assistant/chatbot 212 and/or the treatment data 213/patient data 214 for creating content for the response action 238, which is provided as a text message, multimedia message, email message, etc. to an appropriate clinician account that is associated with resolving alarms. In an example, the response action 238 includes a recorded personal inquiry from the patient (possibly with video or images of the display interface 201 of the therapy machine 90 showing the alarm) in addition to the alarm-based treatment data 213 and/or patient data 214 for additional context.

In instances where the clinician server 204 determines that the patient request is critical or urgent, the clinician server 204 identifies a clinician and establishes a direct communication link between a clinician device 152 of the identified clinician and the personal mobile communication device 122 of the patient. The communication may include a voice call, a video call, and/or an active chat session.

As illustrated in FIG. 2, the example medical system 10 includes a web portal 150 to facilitate the transmission of data to the clinician device 152 and/or the personal mobile communication device 122 via a network 230. The example network 230 may include any wired and/or wireless network, such as the Internet, a cellular network, or combinations thereof. The networks 210 and 230 may include the same network.

The web portal 150 may include one or more application programming interfaces ("API") or other network interfaces that provide for the communication of treatment data 213, patient data 214, and/or response actions 238. The web portal 150 may also establish communication sessions between the clinician device 152 and the personal mobile communication device 122. In some instances, the web portal 150 may be configured as a gateway device and/or firewall such that only authorized users and/or devices may communicate with the clinician server 204 and/or the clinician database 206. Further, the web portal 150 may create a separate session for each connected device 122 and 152.

The clinician device 152 and/or the personal mobile communication device 122 may include a respective application 240 and 242 that is configured to interface with the web portal 150 for communicating with the clinician server 204 and/or the clinician database 206. For example, the application 240 may include one or more user interfaces with data fields that are configured to receive a patient request or question. The application 240 is also configured to operate with a telephone feature of the personal mobile communication device 122 to enable a voice or video call to be routed to the clinician server 204 to interact with the virtual assistant/chatbot 212. The application 242 may also include or provide access to an email service, a text message service, or a multimedia message service to enable a patient to enter information for interacting with the virtual assistant/chatbot 212 and/or clinician device 152.

The application 242 of the clinician device 152 is configured with one or more interfaces for receiving a response action 238 from the clinician server 204. The interfaces also enable a clinician to provide a response to a request or inquiry from the personal mobile communication device 122. The application 242 is also configured to operate with a telephone feature of the clinician device 152 to enable a voice or video call to be received from the personal mobile communication device 122. The application 242 may also include or provide access to an email service, a text message service, or a multimedia message service for viewing and responding to patient inquiries (provided by response actions 238 via the clinician server 204).

In other instances, the applications 240 and 242 are web browsers configured to access one or more web pages via the web portal 150 that are hosted or managed by the clinician server 204. In these other instances, the clinician server 204 provides the user interfaces and corresponding data fields in one or more web pages. A user may interact with the web browser to view or enter desired data. The applications 240 and 242 may also include native control or other installed applications on the devices 122 and 152.

In some instances, the web portal 150 is configured to convert prescribed therapies or programs 202, treatment data 213, and/or patient data 214 from a text-based standard or Health-Level-7 ("HL7") standard (e.g., a medical standard)

to a web-based message (e.g., a HTTP message, an HyperText Markup Language ("HTML") message, an Extensible Markup Language ("XML") message, a JavaScript Object Notation ("JSON") payload, etc.). In other embodiments, the connectivity server 118 is configured to convert HL7 prescribed therapies or programs 202, treatment data 213, and/or patient data 214 from the therapy machine 90 into a text-based or web-based format (e.g., a JSON format) for processing by the clinician server 204 and storage by the clinician database 206.

In the illustrated example of FIG. 2, the example personal mobile communication device 122 and the clinician device 152 include a processor 250 that is in communication with a memory 252 storing instructions. At least some of the instructions define or specify the respective application 240 and 242, that when executed by the processor 250, cause the processor 250 to provide interfaces for handling patient inquiries using the virtual assistant/chatbot 212. The processor 250 may comprise digital and/or analog circuitry structured as a microprocessor, application specific integrated circuit ("ASIC"), controller, etc. The memory 252 includes a volatile or non-volatile storage medium. Further, the memory 252 may include any solid state or disk storage medium.

The example medical system 10 of FIG. 2 may also include a third-party server 260 that is associated with a manufacturer of the therapy machine 90. In some instances, the clinician server 204 determines that a patient inquiry relates to an operation or technical issue with the therapy machine 90. In these instances, instead of sending a message to a clinician, the clinician server 204 transmits a message with the response action 238 to the third-party server 260. The response action 238 may include opening a live communication session or providing a text message, multimedia message, an email, etc. to a call center or other diagnostic center that is related to the third-party server 260.

II. Clinician Server-Virtual Assistant/Chatbot Embodiment

Figure 3:
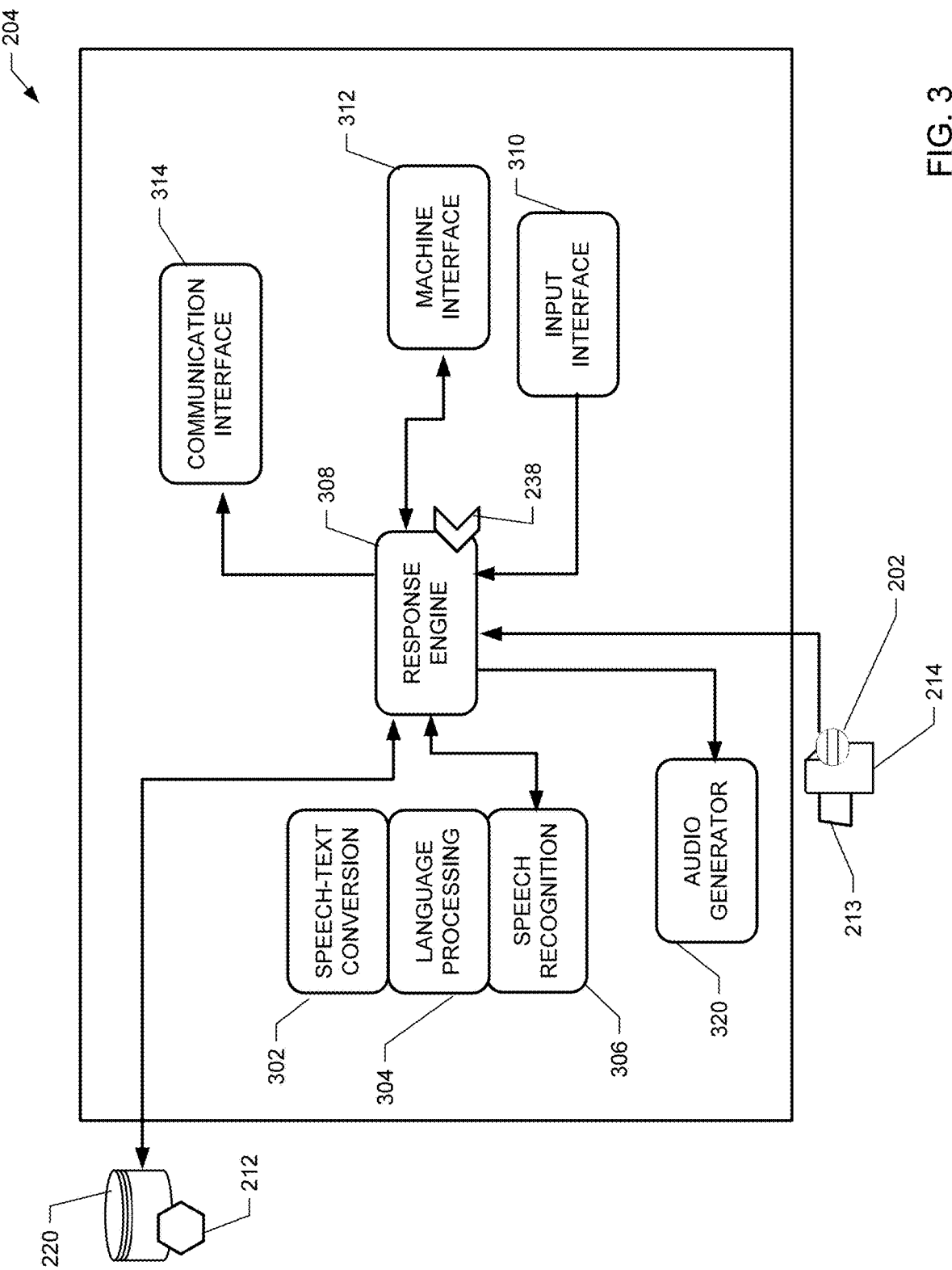
FIG. 3 shows a diagram of the clinician server, according to an example embodiment of the present disclosure.

As discussed above, the example clinician server 204 of FIG. 2 is configured to provide an interactive session with a patient to triage their request. FIG. 3 shows a diagram of the clinician server 204, according to an example embodiment of the present disclosure. In the illustrated example, the clinician server 204 includes instructions or software modules 302 to 320 that specify how the clinician server 204 performs certain operations. The instructions 302 to 320 are used by the clinician server 204 to perform operations of the virtual assistant/chatbot logic 212. The blocks shown in FIG. 3 represent certain operations defined by the instructions 302 to 320. In other embodiments, some of the blocks may be combined, further partitioned, or include additional blocks. Further, while the clinician server 204 is shown as centrally located, in other embodiments, the clinician server 204 and/or the clinician database 206 may be deployed within a cloud computing environment.

The example instructions 302 to 320 include a speech-text conversion module 302, which receives audio or voice commands from the personal mobile communication device 122. The speech-text conversion module 302 receives digital data and/or analog signals that include recorded human speech. The speech-text conversion module 302 is configured to convert the digital data and/or analog signals to text using one or more speech-to-text algorithms.

The speech-text conversion module 302 transmits the converted text to a language processing module 304, which is configured to use one or more algorithms to amend the received text based on known or learned accents, speech, or slang of a user. The language processing module 304 may include a library of known accents, speech, and/or slang for different types of users. The language processing module 304 selects appropriate textual modifiers based on how well a patient matches certain accents, speech, and/or slang. In some instances, the language processing module 304 may use one or more machine learning algorithms for identifying and/or modifying text based on the identified accent, speech, or slang of a user. The language processing module 304 outputs modified text that takes into account a user's accent, speech, or slang. For instance, the language processing module 304 may receive a textual input from the speech-text conversion module 302 that includes combinations of vowels, constants, and breaks. After filtering through the language processing module 304, the string of vowels, constants, and breaks is modified into textual words and/or phrases, which are input into a speech recognition module 306.

The speech recognition module 306 is configured to operate one or more natural language processing algorithms to determine a meaning of received words or phrases. The speech recognition module 306 in some embodiments identifies a meaning of a string of words or phrases, the with identified meaning being stored as metadata, in separate data fields, or otherwise appended to the words and/or phrases. The speech recognition module 306 may analyze words or phrases to identify that a question is being asked, and a subject of the question. In this example, the speech recognition module 306 appends that the words or phrases correspond to a question and keywords that are associated with the question. The processing performed by the speech recognition module 306 adds formatted information that enables subsequent analysis based on more defined linguistic parameters.

In some embodiments, the speech recognition module 306 is configured to search for certain keywords for starting a virtual session with a patient. If a virtual session is not already in progress, the speech recognition module 306 listens or otherwise processes text and phrases for certain keywords or phrases that are indicative to start a session. For example, the virtual assistant/chatbot may be called "Claria". Accordingly, the speech recognition module 306 searches for the term "Claria" or similar spellings. If a match is made, the speech recognition module 306 begins a virtual session with a patient and processes the phrase that includes the "Claria" term. At this point, the speech recognition module 306 processes subsequent words and/or phrases as part of the virtual conversation. However, if a match is not made, the speech recognition module 306 discards the text from further processing so as to refrain from recording other patient conversations or ambient room sounds. It should be appreciated that the virtual assistant/chatbot 212 may also be activated by a patient by selecting a corresponding icon that is displayed by the user interface 201 of the therapy machine 90 or the application 240 of the personal mobile communication device 122.

The example clinician server 204 also includes a response engine 308 that is configured to apply text from the speech recognition module 306 and/or the data 202, 213, and/or 214 to the virtual assistant/chatbot logic 212. The potential inputs into the response engine 308 accordingly include text from the speech recognition module 306 and/or text from a chatbot program provided by the user interface 201 of the therapy machine 90 or the application 240 of the personal mobile communication device 122. The inputs also include the prescribed therapy or program 202, the treatment data 213, and/or the patient data 214.

The example adaptive interface 308 includes an input interface 310 that is configured to receive text and/or other inputs entered into the user interface 201 of the therapy machine 90 or the application 240 of the personal mobile communication device 122. The inputs may include selection of an icon that causes the adaptive interface 308 to begin a virtual interactive session with a patient. The inputs may also include text that is entered into a chat session via the user interface 201 of the therapy machine 90 or the application 240 of the personal mobile communication device 122. In some instances, the response engine 308 launches a virtual chat session by opening a virtual chat or text messaging session on the user interface 201 of the therapy machine 90 or the application 240 of the personal mobile communication device 122. Text entered by a user into a field or text box is transmitted by the user interface 201 of the therapy machine 90 or the application 240 of the personal mobile communication device 122 to the response engine 308 via the input interface 310. In some instances, the input interface 310 may include one or more application programming interfaces ("APIs") that connect to the text messaging application, which enable routing of entered text to the response engine 308. In addition to text, the input interface 308 may accept images, video, emojis, or selection indications of displayed options.

To receive the treatment data 213 from the therapy machine 90, the server 204 includes a machine interface 312. The example memory interface 312 is configured to request or otherwise receive the treatment data 213 from the therapy machine 90. In some embodiments, the adaptive interface 308 is configured to use the machine interface 312 to request the treatment data 213 after detecting that a patient has begun a virtual interactive session. In another embodiments, the adaptive interface 302 may search the clinician database 206 for relevant treatment data 213 and/or patient data 214 (and a prescribed therapy or program) using the machine interface 312 when the virtual assistant/chatbot logic 212 is configured to use certain medical information for answering a question, determining a response action 238, or otherwise creating content for a response action 238.

Figure 4:
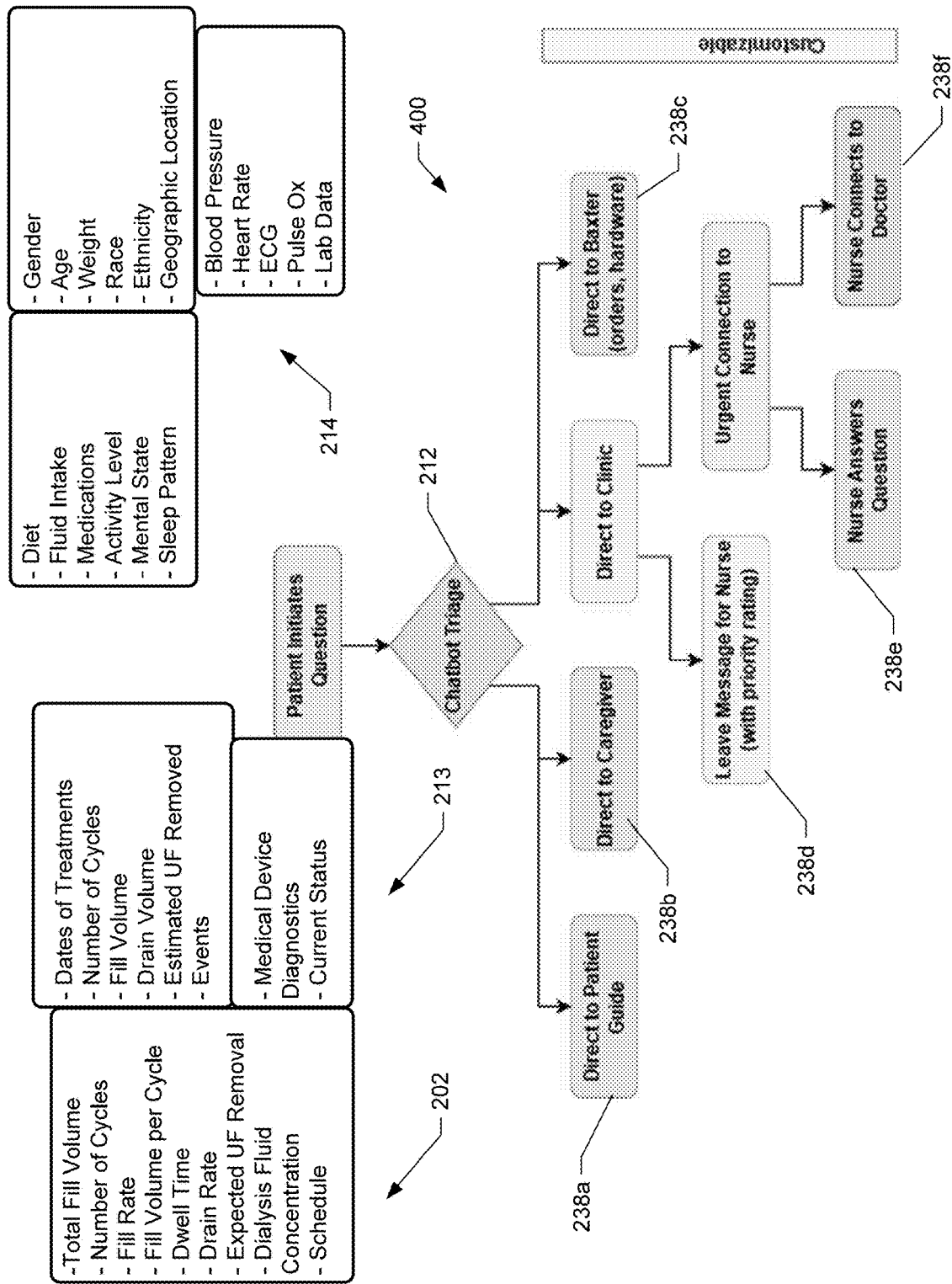
FIG. 4 is a diagram of a process performed by virtual assistant/chatbot logic for triaging a patient inquiry, according to an example embodiment of the present disclosure.

FIG. 4 is a diagram of a process 400 performed by the virtual assistant/chatbot logic 212 for triaging a patient inquiry, according to an example embodiment of the present disclosure. The example process 400 begins when a patient initiates a query using the application 240 on the personal mobile communication device 122 and/or the display interface 201 of the therapy machine 90. The virtual assistant/chatbot logic 212 and uses logic to select one or more follow up questions. In other words, the virtual assistant/chatbot logic 212 provides an interactive session to progress through a hierarchy of questions with one or more prompts to receive further information until a response action 238 is identified. In some embodiments, the hierarchy of requests/answers/questions of the virtual assistant/chatbot logic 212 may be modified based on protocols of a hospital system or clinic.

Figure 5:
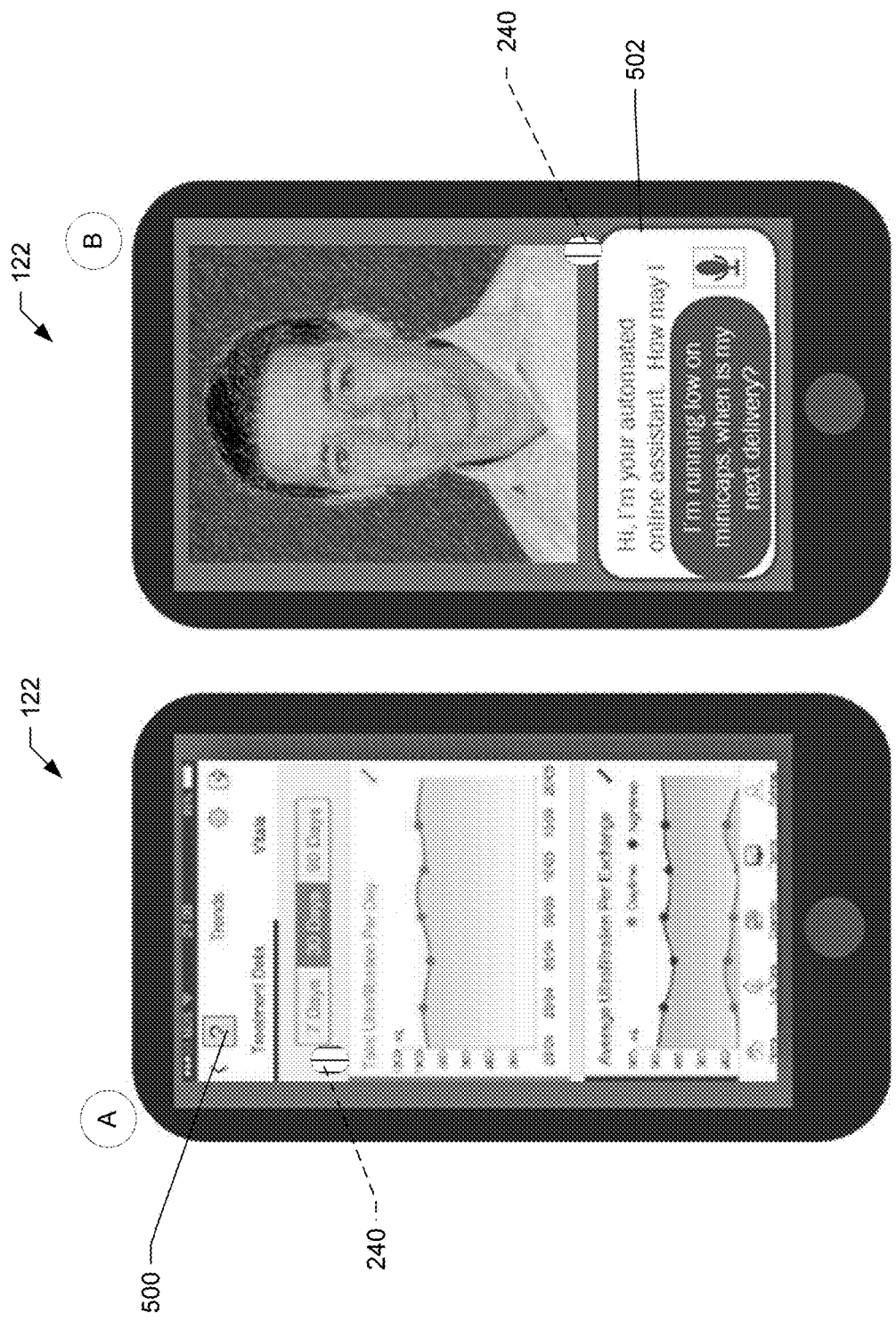
FIG. 5 is a diagram that shows an interface of an application provided on a personal mobile communication device, according to an example embodiment of the present disclosure.

FIG. 5 is a diagram that shows an interface of the application 240 provided on the personal mobile communication device 122, according to an example embodiment of the present disclosure. At Event A, the application 240 displays at least some treatment data 213 including ultrafiltration trends. The interface includes an icon 500 that enables the patient to initiate the virtual assistant/chatbot logic 212. Event B shows the application displaying an interactive interface 502 for the virtual assistant/chatbot logic 212. The interactive interface 502 includes automated text from the virtual assistant/chatbot logic 212 asking a patient for their issue or question. As shown, the patient types or speaks that they are running low on minicaps (i.e., a PD disposable item). The interactive interface 502 may also display a picture of a generic virtual assistant or a picture of the patient's clinician. The text or speech provided by the patient is processed by the clinician server and/or the virtual assistant/chatbot logic 212, as discussed above.

The virtual assistant/chatbot logic 212 includes listing of possible issues and keywords associated with the issues. The response engine 308 in conjunction with the virtual assistant/chatbot logic 212 perform keyword matching to determine which issue a patient is likely referring. In the example, above, a patient indicates that help is needed with an alarm, but fails to identify the type of alarm (e.g., an occlusion alarm, a dialysis fluid leakage alarm, a low container alarm, a pumping alarm, a overfill alarm, etc.). In this instance, the virtual assistant/chatbot logic 212 specifies keywords associated with each alarm type. Instead of asking the patient more questions, the response engine 308 uses the treatment data 213 to determine that an occlusion alarm is active. This additional piece of information enables the response engine 308 and/or the virtual assistant/chatbot logic 212 to determine that the issue relates to an occlusion alarm.

The virtual assistant/chatbot logic 212 includes a data structure of possible issues. Each issue has one or more keywords that are related to the issue. The keywords are preselected based on an analysis of the data 202, 213 and/or 214 and patient responses from a population of patients related to the issue. For example, an issue for an occlusion alarm includes keywords such as "alarm, alert, noise, flashing, beeping, and warning". The keywords may also include diagnostic identifiers generated by the therapy machine 90 (and included in the treatment data 213) associated with an occlusion detection. These keywords may include diagnostic trouble codes, field identifiers for occlusion detection, or event identifiers.

The virtual assistant/chatbot logic 212 is configured to compare the received text and data 202, 213, and/or 214 to each of the higher-order issues. The virtual assistant/chatbot logic 212 selects an issue with a greatest matching score or probability based on the comparison with the keywords. The virtual assistant/chatbot logic 212 may prevent a selection if a match does not exceed a match threshold, such as 60% or 75%. In this instance, the virtual assistant/chatbot logic 212 includes follow up questions to ask the patient based on which issues have the greatest matching scores.

The virtual assistant/chatbot logic 212 may include a hierarchy of questions and answers for at least some of the possible issues. These additional questions and answers may further refine an issue to a more precise issue to provide a better resolution. For example, a higher-order issue may refer just to alarms. The lower level questions and answers provide keywords and criteria of different types of alarms. In some instances, the answers may be determined directly from the data 202, 213, and/or 214 without further input from the patient, as in the occlusion alarm example discussed above. However, if any of the lower level answers cannot be determined, the virtual assistant/chatbot logic 212 uses the listed questions associated with each possible answer of a higher-level issue for selecting which questions are provided to the patient for follow up. The hierarchy of the virtual assistant/chatbot logic 212 provides an issue/sub-issue transversal that causes the response engine 308 to quickly converge upon a likely issues experienced by the patient for determining the response action 238.

At some point in the hierarchy, answers for a sub-issue are associated with the response action 238. The virtual assistant/chatbot logic 212 determines when there is a match or likely match above a threshold with a response action 238. Based on this match, the response engine 308 transmits the response action 238 to the patient and/or an identified clinician. In some instances, a response action 238 may be provided for higher-level issues without needing to progress through a hierarchy of sub-issues. The virtual assistant/chatbot logic 212 accordingly defines how the response engine 308 is to interact with a patient to identify which issue is being experienced by a patient.

As shown in FIG. 4, there are a number of different possible response actions 238 based on a determined criticality level. In some embodiments, the virtual assistant/chatbot logic 212 may have three levels. In other embodiments, there may be fewer or greater levels. In a three-level configuration, a lowest level corresponds to basic patient questions or requests that can be automatically answered without human intervention. These includes questions/requests about a patient's guide, supply reordering, and/or general information about the therapy machine 90. A medium-level corresponds to a request/patient question for a clinician to address as their time permits, thereby not interrupting the clinician's workflow. These questions or requests can relate to mild or moderate medical issues and/or infrequent issues with the therapy machine 90. A critical-level corresponds to questions/requests that need to be answered by a clinician immediately. These response actions 238 are flagged, prioritized, and escalated by the clinician server 204. These questions/requests or patient inquiries may relate to peritonitis, fluid status, and frequent or ongoing issues with the therapy machine 90.

FIG. 4 also shows at least some of the prescribed therapy or programs 202, treatment data 213, and/or patient data 214 that may be used by the virtual assistant/chatbot logic 212 to more quickly converge upon the response action 238 or create content for the response action 238. The prescribed therapy or programs 202 includes treatment parameters that be defined in one or more dialysis prescriptions or programs. For PD, the prescribed therapy or programs 202 may include one or more of a total fill volume, a number of cycles, a fill rate, a fill volume per cycle, a dwell time, a drain rate, an expected ultrafiltration ("UF") removed per cycle or treatment, a dialysis fluid concentration (e.g., dextrose concentration), or a treatment schedule. For HD, the prescribed therapy or programs 202 may specify a treatment time, a blood circulation rate, a dialysis fluid circulation rate, a dialysis fluid volume, a treatment schedule, or a dialysis fluid concentration. For an infusion therapy, the prescribed therapy or programs 202 may include an infusion rate, a volume of fluid to be infused, a fluid type/volume, a drug or component concentration of the fluid, and a total infusion time. The prescribed therapy or programs 202 may be received from the therapy machine 90 and/or the clinician database 206 (as stored in a patient's EMR).

The treatment data 213 describes how a dialysis treatment was performed. As shown in FIG. 4, the treatment data 213 may include for a PD treatment at least one of dates/times that treatments were performed, a number of cycles per treatment, a fill volume, a drain volume, an estimated or measured amount of UF removed, and any events that occurred during a treatment. The events may include an alarm, an alert, a patient entry conflicting with a limit or threshold, a line occlusion, a line leak/disconnection, pausing of a treatment, etc. In some instances, the treatment data 213 may also include physiological data when the therapy machine 90 is connected to or includes one or more sensors, such as a blood pressure sensor or cuff, a weight scale, a heart rate sensor, an ECG sensor, etc. Altogether, the treatment data 213 provides a summary of how a dialysis treatment was performed.

The treatment data 213 may further include device information. For instance, the device information 508 may include a correct status of the therapy machine 90, such as whether the machine is in a priming sequence, a cleaning/disinfection sequence, about to start a cycle of a PD treatment, progressing through a fill phase, progressing through a dwell phase, progressing through a drain phase, or finished with a cycle or treatment. The device information may also include diagnostic information, such as faults detected in one or more pumps, valves, or other dialysis components.

The patient data 214 relates to information specific for patient that cannot be readily determined through monitoring of the therapy machine 90. The patient data 214 may include patient activity information, patient demographic information, and patient medical information. The patient activity information is determined through one or more question and answer sessions with a patient. Additionally or alternatively, the patient activity information may be determined from a patient's EMR.

In an example, a PD treatment may take three or four hours to complete. During this time, a patient is fluidly connected to the therapy machine 90 during at least dialysis fluid fill and drain phases of a cycle, which can be boring for a patient. To help fill the time, the clinician server 204 may be configured to determine from the treatment data 213 that a fill phase will occur for the next 30 minutes. Also, the clinician server 204 is configured to determine from the speech recognition module 306 that the ambient environment is quiet. Based on these conditions, the clinician server 204 may be configured to begin a virtual session with a patient to fill the time to acquire some patient data 214, which may include diet information, fluid intake, medications, activity level, mental state, and sleep pattern. The clinician server 204 may prompt the patient with simple questions, such as "What have you eaten today?", "Which medications have you taken?", "What have you done today?", and "How are you feeling?" and "How did you sleep?". Patient responses are recorded by the clinician server 204 as the patient data 214. The clinician server 204 may timestamp the patient data 214 to enable trends to be determined. In some instances, the clinician server 204 may use the virtual assistant/chatbot logic 212 for asking questions and determining if follow up questions are needed. In addition to asking questions during a treatment, the clinician server 204 may ask questions after a treatment or before a treatment at times that are not likely to interrupt a patient.

In addition to prompting the patient for patient activity information, the clinician server 204 may prompt the patient for the patient demographic information. Alternatively, the clinician server 204 may obtain the patient demographic information from one or more EMRs stored in the clinician database 206. As shown in FIG. 4, the patient demographic information may include gender, age, weight, race, ethnicity, and geographic location. The clinician server 204 may use the virtual assistant/chatbot logic 212 to obtain the patient demographic information from a patient before, during, or after treatments.

The clinician server 204 may also prompt a patient for the patient medical information using the same virtual session. Alternatively, the clinician server 204 may use the therapy machine 90 to obtain at least some of the patient medical information using a connected physiological sensor. In yet other instances, the clinician server 204 obtains the patient medical information of the patient data 214 from one or more EMRs. Altogether, the patient data 214 provides a summary of a health of a patient that may include at least some subject information that is obtained through a virtual session.

As shown in FIG. 4, the process 400 includes triaging the patient request into an appropriate response action 238. A first response action 238*a* corresponds to providing an automated response to a patient. The first response action 238*a* is selected for designated low-level inquires. The responses reference certain sections of medical and/or product documentation and/or sections of the patient data 214 (e.g., a patient's EMR). The clinician server 204 copies the information and includes the information in one or more response messages as the response action 238*a*. The messages may be conveyed as a text or multimedia message, a voice message, and/or an audiovisual message. The following questions and responses may be provided via the response action 238*a*:

Example 1: Question can be answered by Chatbot and/or Patient Guide
    "How do I connect my new solution bag?"
    Answer with Information on page 93 of a Patient Guide
    Chatbot replies and closes the call
    Example 2: routine but patient-specific question
    "I'm running low on Minicaps, when is my next delivery?"
    Something with clear yes/no that can be answered easily.
    Chatbot answers directly—easy question for a database to answer.

Response actions 238*b*, 238*e*, and 238*f* of FIG. 4 corresponds to critical-level responses. Here, the clinician server 204 determines that a patient needs to be placed in contact with a clinician, nurse, or doctor. The clinician server 204 uses the virtual assistant/chatbot logic 212 in conjunction with the patient responses and the data 202, 213, and/or 214 to determine which practitioner is best able to handle the response in addition to determining the criticality of the response. After identifying an individual, the clinician server 204 determines their phone number or virtual identifier in an electronic address book to establish a communication session. The clinician server 204 may include a communication interface 314 to establish a voice call, a video call, a conference call, and/or a live text session. The communication interface 314 may transmit one or more messages to the identified clinical device 152 and the personal mobile communication device 122 to establish the session via the respective response action 238*b*, 238*e*, or 238*f*. In some embodiments, the communication interface 314 adds content for the response action 238 for viewing on the application 242 of the clinician device 152. The content may include information provided by the patient during the virtual session, and/or relevant portions of the data 202, 213, and/or 214. Below is an example interaction.

Example 3: Urgent question, sent directly to nurse immediately
    "My stomach hurts and my effluent is cloudy. What do I do?"
    Contacts nurse with urgent note/escalation of message; and tell patient to come in In some embodiments, the clinician server 204 selects the response action 238*c* for messages to a manufacturer of the therapy machine 90. The response action 238*c* may include a text message, voicemail, email, etc. that can be addressed in time by a call center of the manufacturer. In some urgent instances, the clinician server 204 establishes a live session, as discussed above. Below is an example interaction.

Example 4: Question can be answered by Chatbot
    "There is something floating in my new solution bag, what should I do?"
    Answer with "Don't use it; I will connect you with Product Surveillance"
    Chatbot replies and closes the call FIG. 4 also shows response actions 238*d* where a message is provided to a clinician. In these instances, the clinician server 204 constructs an email, text message, voice message, etc. that includes some information determined from the virtual interaction with the patient and/or the data 202, 213, and/or 214. Further, the clinician server 204 may prompt the patient to leave a voicemail or other text for the clinician. In these examples, the clinician server 204 uses the communication interface 316 to transmit the response action 238*d* to an appropriate communication account of the clinician. Below is an example interaction.

Figure 6:
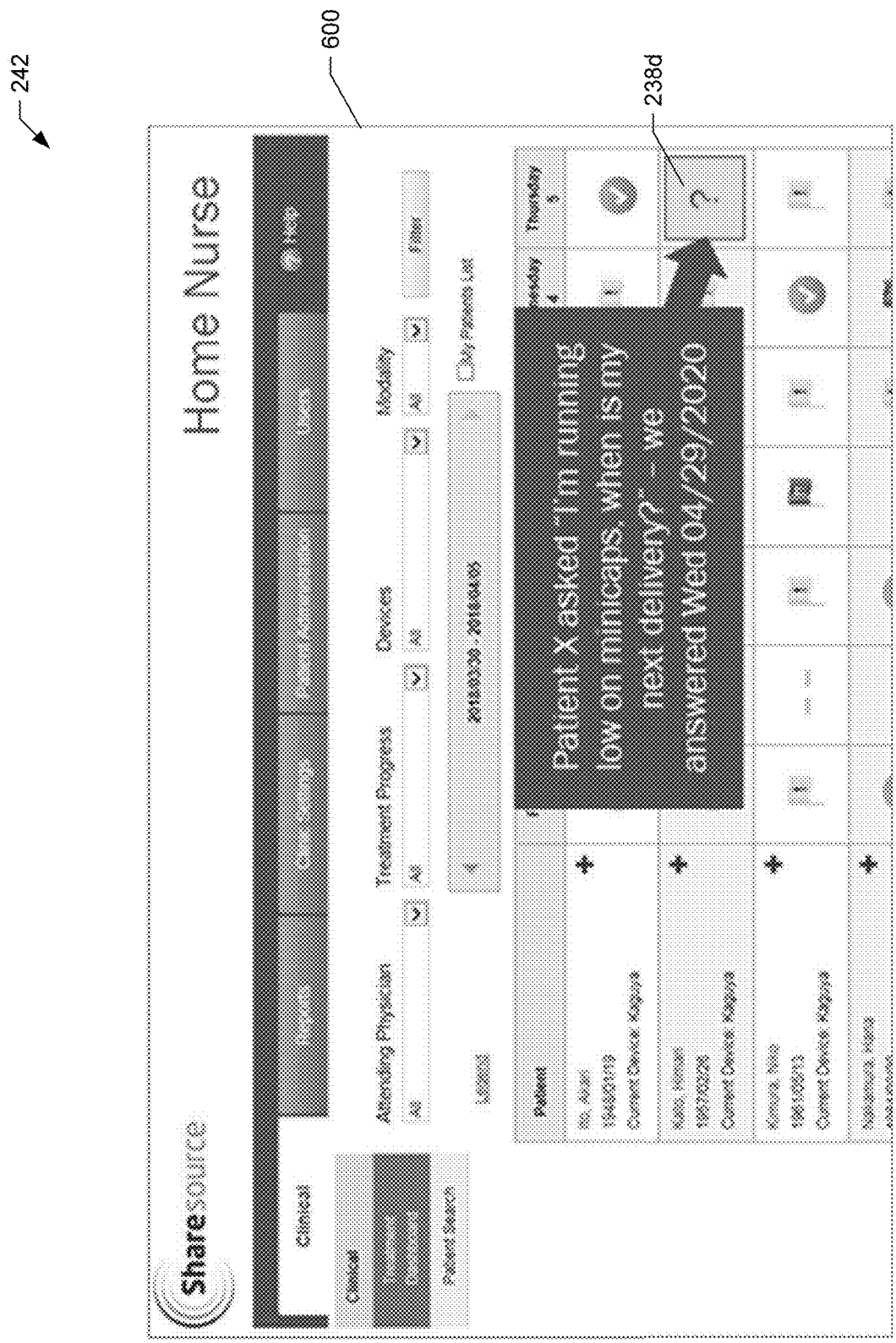
FIG. 6 is a diagram of a dashboard provided by a clinician application for responding to response actions, according to an example embodiment of the present disclosure.

Example 5: Harder question to answer, leave a voicemail with clinic that is given a prioritization score. Can't be answered with patient guide but not urgent.
    "I'm doing my 24 hour collection soon and I forgot how to do it; can you help?"
    Nurse will get a message and can call back later with instructions FIG. 6 is a diagram of a dashboard 600 provided by a clinician application 242 for responding to the response actions 238*d*, according to an example embodiment of the present disclosure. The dashboard 600 shows a list of patients and response actions 238*d* associated with each patient by day. The dashboard 600 is configured to enable the clinician to select a response action 238*d*. In response to a selection, the dashboard 600 of the application 242 provides an interface for a clinician to type or record a response, which is then transmitted via the clinician server 204 to the application 240 of the personal mobile communication device 122.

The dashboard 600 also provides indications as to which response actions 238*d* have been addressed. In some embodiments, the dashboard 600 changes a color of an icon or otherwise promotes a response action 238*d* to gain a clinician's attention if a response is not provided within a threshold time period, such as two hours, four hours, six hours, twelve hours, 24-hours, 48-hours, etc. Further, if a response action 238*d* has not been addressed within the threshold, the clinician server 204 may provide the response action 238*d* to the dashboard of other clinicians. The dashboard 600 may also enable a clinician to route a response action 238*a* to another clinician.

III. Conclusion

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A virtual assistant/chatbot system to improve clinical workflows for home renal replacement therapies, the system comprising:

an interface communicatively coupled to a network, the interface configured to communicate with an application on user devices or an interface for medical devices;

a memory device storing a patient inquiry triage data structure for a virtual assistant or chatbot, the data structure including a plurality of potential issues related to dialysis or operation of a medical device, wherein the medical device includes at least one of a peritoneal dialysis machine, a hemodialysis machine, a continuous renal replacement therapy ("CRRT") machine, an infusion pump, or a patient-controlled analgesia ("PCA") machine, each issue including a hierarchy of questions and possible answers that lead to a response action, the response action including a direct communication connection with a clinician and a communication connection with a voice mail system, a person-to-person chat system, or an email system; and a processor communicatively coupled to the interface and the memory device, the processor configured to receive an inquiry message from the application on a user device or the interface of the medical device, provide an interactive session using the virtual assistant or chatbot to progress through the hierarchy of questions with one or more prompts to receive further information until a response action is identified, when the response action is related to direct communication, determine an address or number of a clinician device and cause a communication session to be initiated between the application on the user device or the interface of the medical device and the clinician device, and when the response action is related to the voice mail system, the person-to-person chat system, or the email system, determine an account of a clinician and enable the patient to use the application on the user device or the interface of the medical device to send a request message for a clinician.

2. The system of claim 1, wherein the processor is further configured to incorporate at least some of the further information from the interactive session with the request message for the clinician.

3. The system of claim 1, wherein the processor, the memory device, and the interface are located in a cloud-computing environment.

4. The system of claim 1, wherein the inquiry message and the further information is received as speech, and the processor is configured to convert the speech to text.

5. The system of claim 1, wherein the processor is further configured to:
receive a clinician response message from the account of the clinician for the voicemail system, the person-to-person chat system, or the email system; and
transmit the clinician response message to the application on the user device or the interface of the medical device.

6. The system of claim 1, wherein the response action further includes an automated response action, and
when the response action is related to the automated response action, the processor is configured to transmit information indicative of the automated response action to the application on the user device or the interface of the medical device.

7. The system of claim 6, wherein the automated response action includes at least one of an answer from a patient guide, an answer about an order for a medical device consumable item, an answer related to an operation of the medical device, or a preprogrammed answer related to general patient health or medical conditions.

8. The system of claim 1, wherein the response action further includes a medical device manufacturer response action, and
when the response action is related to the medical device manufacturer response action, the processor is configured to determine an address or number of a manufacturer device and cause a communication session to be initiated between the application on the user device or the interface of the medical device and the manufacturer device.

9. The system of claim 8, wherein the medical device manufacturer response action relates to at least one of reordering consumables for the medical device, a technical issue with the medical device, or an operational issue with the medical device.

10. The system of claim 1, wherein the processor is further configured to:
access at least one of treatment data from the medical device or patient data related to the patient from an electronic medical record after receiving the inquiry message; and
use at least some of the treatment data or the patient data as answers for progressing through the hierarchy of questions as part of the interactive session.

11. The system of claim 1, wherein the processor is further configured to:
access at least one of treatment data from the medical device or patient data related to the patient from an electronic medical record after receiving the inquiry message; and
include at least some of the treatment data or the patient data with the request message for the clinician.

12. The system of claim 11, wherein the treatment data includes at least one of (i) treatment parameters for a dialysis prescription, (ii) results from performing one or more dialysis treatments, (iii) diagnostic information related to the medical device, or (iv) a current status of the medical device, and
wherein the patient data includes at least one of electronic medical record information, laboratory results, electronic clinician notes, previous medical diagnoses, patient physiological data, or patient demographic data.

13. The system of claim 1, wherein a hierarchy of the patient inquiry triage data structure is configured to be modified based on protocols of a hospital system or clinic.

14. A virtual assistant/chatbot method to improve clinical workflows for home renal replacement therapies, the method comprising:
receiving, in a processor, an inquiry message from an application on a user device or an interface of a medical device, wherein the medical device includes at least one of a peritoneal dialysis machine, a hemodialysis machine, a continuous renal replacement therapy ("CRRT") machine, an infusion pump, or a patient-controlled analgesia ("PCA") machine;
providing, via the processor, an interactive session using a virtual assistant or chatbot to progress through a hierarchy of questions with one or more prompts to receive further information until a response action is identified, instructions for the virtual assistant or chatbot being stored in a memory device that also stores a patient inquiry triage data structure for the virtual assistant or chatbot, the data structure including a plurality of potential issues related to dialysis or operation of the medical device, each issue including the hierarchy of questions and possible answers that lead to a response action, the response action including a direct communication connection with a clinician and a communication connection with a voice mail system, a person-to-person chat system, or an email system;

when the response action is related to direct communication, determining, via the processor, an address or number of a clinician device and causing a communication session to be initiated between the application on the user device or the interface of the medical device and the clinician device;

and when the response action is related to the voice mail system, the person-to-person chat system, or the email system, determining an account of a clinician and enabling the patient to use the application on the user device or the interface of the medical device to send a request message for a clinician.

15. The method of claim 14, further comprising incorporating, via the processor, at least some of the further information from the interactive session with the request message for the clinician.

16. The method of claim 14, wherein the inquiry message and the further information are received as speech, and the method further includes converting the speech to text.

17. The method of claim 14, further comprising:
receiving, in the processor, a clinician response message from the account of the clinician for the voicemail system, the person-to-person chat system, or the email system; and
transmitting, via the processor, the clinician response message to the application on the user device or the interface of the medical device.

18. The method of claim 14, wherein the response action further includes an automated response action, and when the response action is related to the automated response action, the method further includes transmitting information indicative of the automated response action to the application on the user device or the interface of the medical device.

19. The method of claim 18, wherein the automated response action includes at least one of an answer from a patient guide, an answer about an order for a medical device consumable item, an answer related to an operation of the medical device, or a preprogrammed answer related to general patient health or medical conditions.

20. The method of claim 14, further comprising:
accessing, via the processor, at least one of treatment data from the medical device, a prescribed therapy or program, or patient data related to the patient from an electronic medical record after receiving the inquiry message; and
including, via the processor, at least some of the treatment data, the prescribed therapy or program, or the patient data with the request message for the clinician,
wherein the prescribed therapy or program includes treatment parameters for a dialysis prescription, the treatment data includes at least one of (i) results from performing one or more dialysis treatments, (ii) diagnostic information related to the medical device, or (iii) a current status of the medical device, and
wherein the patient data includes at least one of electronic medical record information, laboratory results, electronic clinician notes, previous medical diagnoses, patient physiological data, or patient demographic data.

* * * * *